US00PP09743P

United States Patent [19]

Dümmen

[11] Patent Number: Plant 9,743

[45] Date of Patent: Dec. 10, 1996

[54] GERANIUM PLANT NAMED HWD CAMPANA

[75] Inventor: Günter Dümmen, Rheinberg-Eversael, Germany

[73] Assignee: Dummen Jungpflanzenkulturen, Rheinberg-Eversael, Germany

[21] Appl. No.: 517,102

[22] Filed: Aug. 21, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of geranium plant named HWD Campana, characterized by its semi-double purple flowers; compact plant size; freely branching habit; and a large number of umbels per plant.

1 Drawing Sheet

The present invention relates to a new and distinct cultivar of geranium plant, botanically known as *Pelargonium×hortorum,* known as the variety Duecampa, and hereinafter referred to by the cultivar name HWD Campana.

The new cultivar is a product of a planned breeding program conducted by the inventor in Rheinberg, Germany. The objective of the breeding program was to develop a new early-flowering, semi-double geranium with purple-colored flowers.

The new cultivar originated from a cross made by the inventory of the proprietary selection 86-40-10 as the male or pollen parent with the proprietary selection 87-31-9 as the female or seed parent.

The cultivar HWD Campana was discovered and selected by the inventor as a flowering plant within the progeny of the stated cross in controlled environment in Rheinberg, Germany. Asexual reproduction of the new cultivar by terminal cuttings taken at Rheinberg, Germany, has shown that the unique features of this new geranium are stabilized and reproduced true to type in successive generations of asexual reproduction.

The following traits have been repeatedly observed and are determined to be the unique characteristics of HWD Campana. These characteristics in combination distinguish HWD Campana as a new and distinct cultivar:

1. Semi-double purple flowers.
2. Compact plant size.
3. Freely branching.
4. Large number of umbels per plant.

In comparison to the parent selection 86-40-10, plants of the new geranium have more umbels per plant, but umbels are smaller in size. In comparison to the parent selection 87-31-9, plants of the new geranium have more umbels per plant, but plants are more compact in size.

The new geranium is most similar to the nonpatented cultivar Penve. In comparison to the cultivar Penve, plants of the new geranium have more umbels per plant, but smaller umbels. The new geranium is similar in petal color to the patented cultivars Fox (U.S. Plant Pat. No. 7,083); Americana Violet (U.S. Plant Pat. No. 8,750); and Fisino (U.S. Plant Pat. No. 8,761). Compared to plants of the cultivar Fox, plants of the new geranium have lighter green foliage, longer peduncles, pedicels that are green and not red in color, and more umbels per plant. Compared to plants of the cultivar Americana Violet, plants of the new geranium have much larger umbels, longer peduncles, and more umbels per plant. Compared to plants of the cultivar Fisdino, plants of the new geranium have shorter peduncles, fewer flowers per umbel, and less pronounced zoned foliage.

The accompanying colored photograph illustrates the overall appearance of the new cultivar, showing the colors as true as it is reasonably possible to obtain in colored reproductions of this type. Flower color appears more red than the actual flower color due to light reflectance. The photograph comprises a top perspective view of a typical potted plant of HWD Campana with one plant in a 10-cm container.

The cultivar HWD Campana has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical.*—*Pelargonium×hortorum.*

*Commercial.*—Zonal geranium.

*Cultivar.*—'HWD Campana'.

Parentage:

*Male parent.*—Proprietary selection 86-40-10.

*Female parent.*—Proprietary selection 87-31-9.

Propagation:

*Type cutting.*—Terminal cuttings.

*Time to initiate roots.*—Summer: 27° C., 21 days; winter: 20° C., 28 days.

PLANT DESCRIPTION

General appearance: Rounded; compact plant size; upright; freely branching.

Foliage description:

*Arrangement.*—Generally alternate.

*Shape.*—Orbicular with rounded tip and cordate base.

*Size.*—Length: 6.5 to 7.8 cm. Width: 7.5 to 9 cm.

*Texture.*—Velvety; pubescent on upper and under surfaces.

*Margin.*—Crenate.

*Color.*—Young foliage, upper surface: 146A. Young foliage, under surface: 146A. Mature foliage, upper surface: 146A. Mature foliage, under surface: 146A. Zone, upper surface: 147A, not pronounced. Zone, under surface: None. Veins, upper surface: 144B. Veins, under surface: 147C. Petiole: 144A.

*Zonation.*—Width of zone: 1.2 to 1.8 cm. Location of zone: 1 cm from margin and 1.7 cm from petiole.
*Venation pattern.*—Palmate.
*Petiole.*—Length: 5.5 to 7.5 cm. Diameter: 2 mm.

Stem description:
*Internode length.*—0.5 to 1.5 cm.
*Stem color.*—144A.
*Lateral branch number.*—11.
*Lateral branch length.*—7 to 10 cm.

FLOWERING DESCRIPTION

Flowering habit: Freely flowering. Flowers arranged in umbels.

Natural flowering season: Year-round.

Flowers borne: Flower buds develop in apical leaf axils. Umbels are displayed above the foliage.

Quantity of inflorescences: Very floriferous; usually 16 open umbels and at least 5 developing umbels per plant at one time.

Umbels:
*Form.*—Rounded.
*Diameter.*—11 cm.
*Depth (height).*—7 cm.

Flowers:
*Form.*—Semi-double.
*Shape.*—Rounded.
*Quantity of flowers per umbel.*—18 to 20.
*Diameter.*—4.6 to 5 cm.
*Depth (height).*—2 cm.

Petals:
*Shape.*—Obovate with rounded tip.
*Arrangement.*—Rosette, overlapping.
*Quantity.*—5 to 6.
*Aspect.*—Flat.
*Size.*—Length: 2.5 cm. Width: 2.3 cm.
*Texture.*—Satiny, smooth.
*Margin.*—Entire.
*Color.*—When opening, upper surface: 66A. When opening, under surface: 68A. Upper surface: Slightly more violet than 66A. Under surface: 68A. Fading to, upper surface: Base of petals fade to 65C. Venous areas maintain 66A color. Fading to, under surface: No fading observed.

Petaloids:
*Shape.*—Irregular, generally obovate with rounded or clefted tip.
*Arrangement.*—Rosette, overlapping.
*Quantity.*—3 to 5.
*Size.*—Length: 1.8 to 2.2 cm. Width: 1 to 1.8 cm.
*Texture.*—Satiny, smooth.
*Margin.*—Generally entire.
*Color.*—When opening, upper surface: 66A. When opening, under surface: 68A. Upper surface: Slightly more violet than 66A. Under surface: 68A. Fading to, upper surface: Base of petals fade to 65C. Venous areas maintain 66A color. Fading to, under surface: No fading observed.

Peduncle (umbel stem):
*Angle.*—Bent.
*Length.*—16.5 to 18.5 cm.
*Pubescence.*—Very fine.
*Color.*—144A.

Pedicel (individual flower stem):
*Angle.*—Erect, rigid.
*Length.*—3 cm.
*Pubescence.*—Very fine.
*Color.*—59A near sepals, 144A at peduncle.

Flower bud:
*Shape.*—Ovoid.
*Length.*—1.3 cm.
*Diameter.*—7 mm.
*Color.*—66A.

Sepals:
*Arrangement.*—Rosette.
*Quantity.*—5.
*Size.*—Length: 1 to 1.2 cm. Width: 3 to 4 mm.
*Shape.*—Acuminate with apiculate tip.
*Texture.*—Velvety.
*Margin.*—Entire.
*Color.*—Upper surface: 46A at base fading to 144A at tip. Under surface: 46A at base fading to 144A at tip.

Reproductive organs:
*Androecium.*—Stamen number: 12 to 14. Anther size: 1.5 mm. Anther color: 180B. Pollen color: 169B.
*Gynoecium.*—Pistil number: 1 Pistil length: 1 cm. Stigma shape: Decurrent. Stigma color: 64B. Style length: 4 mm. Style color: 64B.

Ploidy level: Tetraploid.

Disease resistance: No fungal, bacterial nor viral problems observed.

Seed Development: Seed production is very rarely observed.

It is claimed:

1. A new and distinct cultivar of geranium plant named HWD Campana, as illustrated and described.

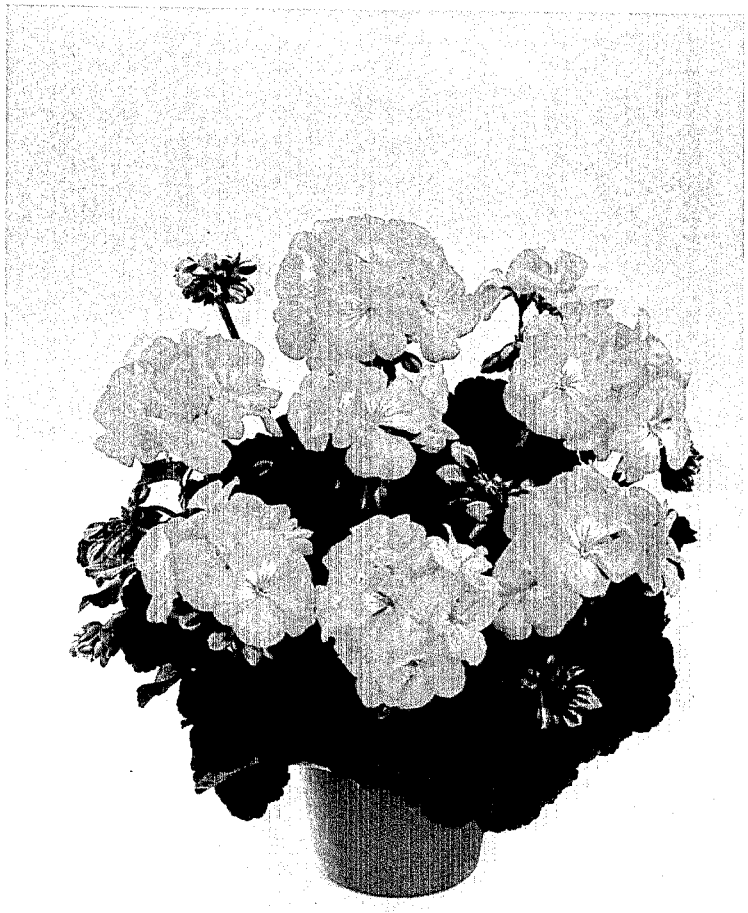

* * * * *